(12) United States Patent
Willett et al.

(10) Patent No.: US 8,215,150 B2
(45) Date of Patent: Jul. 10, 2012

(54) INSTRUMENT DOCKING STATION WITH NON-DESTRUCTIVE SENSOR ANALYSIS CAPABILITIES

(75) Inventors: Martin Willett, Warterlooville (GB); Keith Francis Edwin Pratt, Portsmouth (GB)

(73) Assignee: Life Safety Distribution AG, Uster (CH)

( * ) Notice: Subject to any disclaimer, the term of this patent is extended or adjusted under 35 U.S.C. 154(b) by 583 days.

(21) Appl. No.: 12/389,526

(22) Filed: Feb. 20, 2009

(65) Prior Publication Data

US 2010/0212395 A1   Aug. 26, 2010

(51) Int. Cl.
G01N 27/02 (2006.01)

(52) U.S. Cl. ........................................ 73/1.06; 73/23.21

(58) Field of Classification Search .................. 73/1.02, 73/1.06, 23.21
See application file for complete search history.

(56) References Cited

U.S. PATENT DOCUMENTS

| 5,980,728 | A | * | 11/1999 | Farber et al. ................. 205/784 |
| 6,251,243 | B1 | | 6/2001 | Lindsay ........................ 204/400 |
| 6,442,639 | B1 | | 8/2002 | McElhattan et al. .......... 710/303 |

* cited by examiner

*Primary Examiner* — Hezron E Williams
*Assistant Examiner* — Paul West
(74) *Attorney, Agent, or Firm* — Husch Blackwell LLP

(57) ABSTRACT

A docking station for use with gas sensors includes limited test and diagnostic circuitry directed to specific characteristics of selected detectors. Where a family of detectors is to be evaluated, a universal interface for that family can be included. A single port can be used for multiple different detectors irrespective of specific detector characteristics.

19 Claims, 1 Drawing Sheet

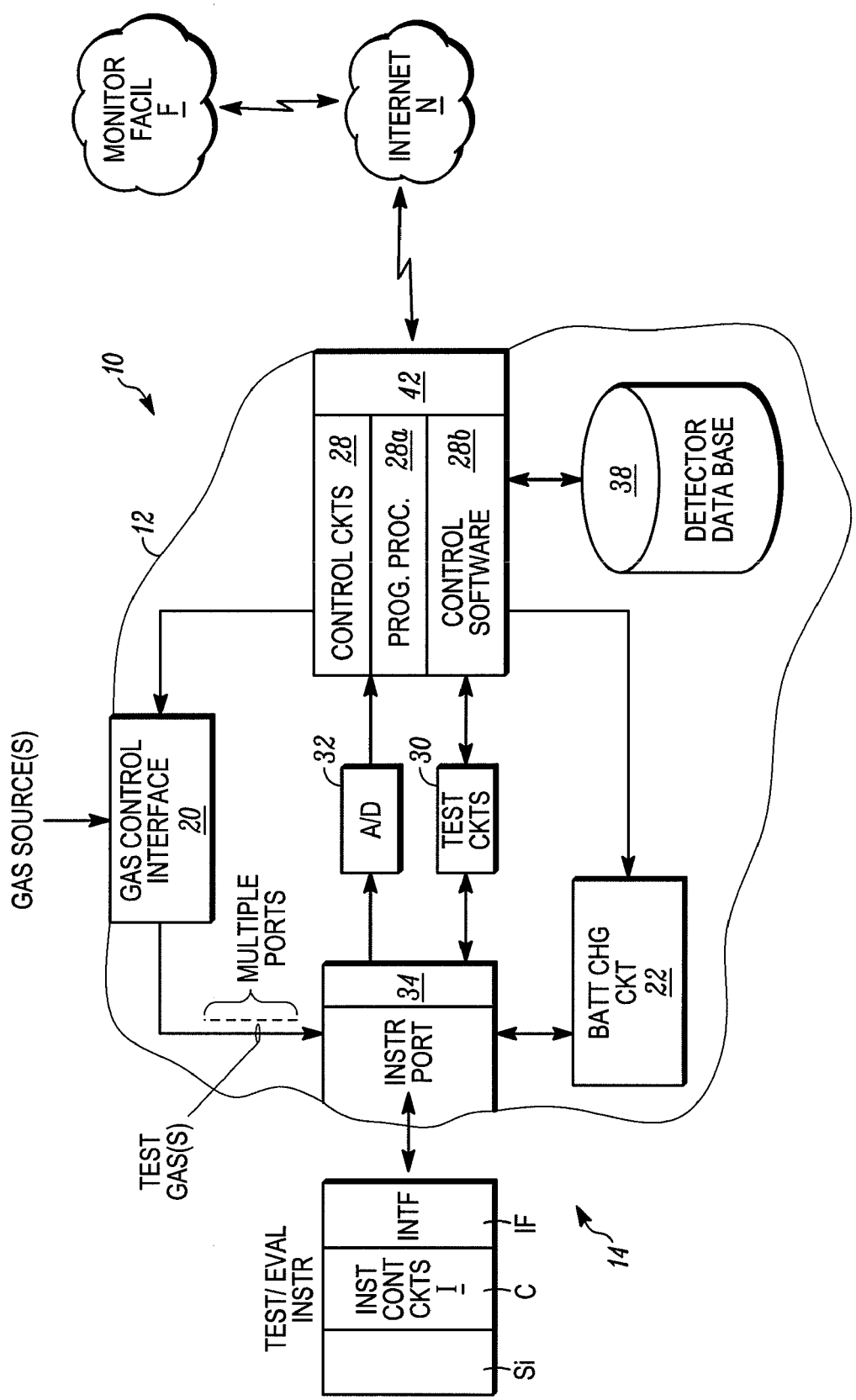

INSTRUMENT DOCKING STATION WITH NON-DESTRUCTIVE SENSOR ANALYSIS CAPABILITIES

FIELD

The invention pertains to ambient condition detectors. More particularly, the invention pertains to docking stations usable to evaluate the condition of portable instruments, which can include electrochemical sensors, so as to identify potential failures prior to the occurrence thereof.

BACKGROUND

Various techniques are known which can provide valuable information as to the performance of gas sensors and potentially facilitate the prediction of impending failure or remaining life. Simple stimulus checks, such as electronic pulsing to confirm the presence of a device or 'bump' testing with gas can be accommodated within instrument hardware and normal operating regimes. However, more sophisticated hardware and software is required to perform other useful tests, especially those requiring analysis of the response to complex electrical waveforms.

There are a number of non-destructive test methods which may be used to provide enhanced information about the status of sensors and their host instruments, for example:

complex AC impedance analysis of electrochemical cells;
sensitivity/temperature profiles and heater resistance measurements of various heated devices (including catalytic and heated metal oxide sensors);
received signal level profiles to analyze the performance of optical sources and detectors (as used for example in small infra red sensors);
AC analysis of electrical circuits to determine drift in key components (for example capacitance changes in high impedance amplifiers); and
AC impedance analysis to determine the status and performance of the battery within the instrument.

Many of the above require hardware and software capabilities which exceed those which can economically be provided in small portable instruments. In many cases the respective sensor is unable to perform normal monitoring functions during the test. This may be due, for example, to a requirement to:

provide a known gas environment or other ambient condition/external stimulus;
disconnect the sensor from the usual measurement or display circuitry;
use relatively high power consumption methods;
allow significant recovery time before the sensor can operate normally;
measure external parameters such as gas flow or pressure;
use processor speeds or memory sizes not available in the instruments;
provide hardware/software having no useful function in 'normal' measurement operation; and
use methods which would be difficult or complex to include in a certified device.

Additionally, the interpretation of some test data can be rendered problematic by large temperature excursions which might be encountered in the field. Performing such tests under relatively controlled conditions is therefore greatly preferred. These and other attributes render such functions inappropriate for inclusion in low cost instrument designs or for routine use during normal instrument operation.

BRIEF DESCRIPTION OF THE DRAWING

FIG. 1 is a block diagram of a docking station which embodies the invention.

DETAILED DESCRIPTION

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

In one aspect of the invention, where various instruments within a manufacturer's line may contain similar sensors, by providing a universal interface for a docking station, sensor tests appropriate to the demands of a particular instrument can be automatically or manually selected. In another aspect of the invention, the type of circuitry required in the docking station will be defined by the preferred test regime. For example, it may include AC impedance circuitry or cyclic voltammetry circuits.

Relative to the former, AC analysis may be undertaken at a limited number of frequencies and fixed amplitude and the AC coupled detection circuitry may be simplified accordingly. Relative to the latter, voltammetry, the scan rate and applied voltage range may be specified in advance, removing the requirement to vary these parameters. Additionally, current ranges may be limited to acceptable sensor response levels. In yet another aspect, by setting limited tolerance ranges for key parameters which provide an overview of the sensor health, a simple check on whether the device should remain in service or not may be provided without a complex de-convolution of the equivalent circuit.

In yet another embodiment of the invention, the test results may be stored, interrogated and used in a variety of ways, depending on the nature of the data and its relationship to sensor parameters of relevance. Information may be retained by the docking station or transferred to the instrument or to a manufacturer's database.

In accordance with the above, trend and other forms of analysis may be undertaken offline if necessary. The test regime may be varied in response to initial results and one or more additional interrogations carried out; this process may be automated or user defined.

In the former case, an 'expert system' may be implemented where the docking station has access to a database of previous sensor tests and can use this to predict the likely implications of any given result, and the need for additional investigation. Actions can be implemented immediately, or relayed to other parts of the organization for further consideration.

As explained above, test and evaluation functionality, based on selectively limiting the implementations thereof, can be cost effectively incorporated into docking stations in accordance with the invention. Examples of possible methodologies which can be incorporated include the following, without limitation, which are described as often practiced and with reduced or limited variations thereof as in accordance with the present invention.

Impedance spectroscopy is an evaluation method widely used for the analysis of electrochemical systems. An AC signal is usually coupled, at various frequencies, to the system under test. The real and imaginary components of the resulting signal are measured. Alternately, other approaches such as analysing the decay transient from a pulsed signal can also be used. The system being analysed can be expressed in terms of an equivalent circuit and allows individual measurement of factors relating to, for example, electrodes, electrolyte, mass transport, etc. This methodology is applicable to many types of sensors including wet electrochemical, sensors of toxic gases, oxygen sensors, solid state electrochemical sensors including high temperature zirconia oxygen sensors, resistive metal oxide sensors such as tin dioxide sensors. It can also be used for diagnosis of battery faults.

A number of commercially available 'electrochemical workstation' systems are available which implement the above described processing. They are available, for example, under the Ecochemie, EG+G, or Solartron brand names, as well as others. These devices are ideal for sensor development but are greatly over specified for a simple diagnostic technique. They are expensive and typically cost thousands to tens of thousands of dollars, and, are comparable in size to a desktop PC. Such instruments are capable of working over a wide range of current (e.g. nano or pico amps up to amps) and voltage (millivolts to tens of volts), with operating frequencies for impedance spectroscopy ranging from megahertz to millihertz.

The above described instruments can not cost effectively be incorporated into docking stations. However, as explained below, circuitry in accordance with the invention, which implements a reduced, or limited version of the above, can be incorporated into such docking stations.

For a specific sensor type, typically a relatively small range of current and voltage is required, for example single voltage and current ranges in the millivolt and microamp regions may be sufficient, thereby greatly reducing the cost of the measurement electronics. Measurements at extremely high and low frequencies are less likely to be required. Analysis of the signal may not need to be as sophisticated as that available in a benchtop instrument, for example it may only be necessary to record the magnitude of the signal rather than its real and imaginary components, or the accuracy of the measurement may not need to be particularly high. However the requirements, both in terms of hardware and software are still greater than is typically present in a portable instrument. For example the instrument may only have the ability to take relatively slow readings (e.g. tens of readings per second) and the circuitry may be deliberately bandwidth limited to reduce noise.

Many handheld instruments do implement a very simple 'impedance' measurement as disclosed in U.S. Pat. No. 6,251,243, entitled Gas Detecting Apparatus Having Condition Monitoring Means. However the amount of information extracted from the test is typically quite limited. One docking station implementation, in accordance with the invention, utilizes the existing sensor control circuitry and pulse generator of the type disclosed in the '243 patent but with additional higher speed measurement circuitry and/or signal processing ability incorporated into the docking station. In addition to performing diagnostics on the sensor(s), as described above, impedance spectroscopy could also be used to perform diagnostics on the instrument's battery.

Embodiments of the invention can provide a capability to correct for heater drift in high temperature sensors. Many sensors are required to operate at elevated temperatures and contain heaters, for example metal oxide (tin oxide) type sensors, catalytic bead 'pellistors' or high temperature zirconia sensors. Often the temperature needs to be very precisely controlled.

A common method of heating such devices is to use a metal such as platinum, in either a wire coil, screen printed or photolithographically deposited form. The well defined temperature coefficient of such heaters allows the temperature to be actively controlled by adjusting the power to the heater such that the heater resistance has a specified value relative to its value measured at some reference temperature (typically ambient temperature—a 'cold' resistance measurement). Although the reference resistance can be measured accurately at a well defined temperature during manufacture, drift can occur in the value over time. In practice it has been observed that, although the absolute heater resistance drifts, the temperature coefficient remains relatively constant. Therefore if the reference resistance can be re-measured occasionally, drift in temperature can be compensated for, either by readjusting the heater to the correct value based on the ratio of 'hot' to 'cold' resistance, or by applying a correction factor to the measured sensor signal, or a fault indicated when the temperature has drifted by more than a certain amount. This requires both an accurate measurement of the 'cold' resistance as well as the ambient temperature.

The circuitry required to perform the above described type of measurement may be more sophisticated than that typically present in portable instruments. For example the heater resistance may be controlled by an analogue Wheatstone bridge type circuit or an equivalent digital circuit which has the ability to maintain the heater at a fixed operating resistance but does not have the ability to measure that resistance. Therefore it would be beneficial to have additional external measuring circuitry within the docking, or, base station to perform the required measurements. Since the heater resistance may need to be controlled to within 0.1% or better for some applications, it would also be desirable to be able to perform diagnostics on the heater control circuitry to detect/compensate for drift in the value of reference resistors or offset voltages of operational amplifiers.

Embodiments of the invention can cost effectively vary sensor operating parameters to obtain diagnostic information. It has been recognized that useful information can be obtained from a number of sensor types by varying their operating parameters in a well defined way. For example, by varying the bias voltage of electrochemical sensors, their signal in the presence of a target gas varies in a well defined way and gives information about the sensor performance. Such measurements may require the application of target gas, or in some cases can be performed in ambient air—for example tests on oxygen sensors where the target is always present.

The analysis of the bias voltage dependence of electrochemical sensors is typically performed using linear sweep or cyclic voltammetry. Bench-top or laboratory instrumentation required to perform such measurements is similar to that described above for Impedance Spectroscopy but without requiring frequency analysis. As before, the range of voltage and current available in such instrumentation can not cost effectively be incorporated into docking stations.

Known instruments with 3-electrode sensors typically incorporate potentiostat-type circuitry as would be understood by those of skill in the art. A variable voltage can be fed into the circuitry, to perform measurements at varying bias voltages of a 3-electrode sensor which is already potentiostatically controlled. However 2-electrode sensors, such as oxygen cells are often operated by connecting them across a load resistor and would therefore need to be disconnected from their respective measuring circuits in the instrument and coupled to a more sophisticated circuit, which could be in the docking station.

In an aspect of the invention, the existing current measurement/data acquisition circuitry in the instrument can be used as readings will be of similar magnitude to those measured during normal operation. Further, the bias voltage can be expected to be scanned/stepped relatively slowly in such instruments.

For heated sensors such as metal oxide sensors or pellistors, variation of the sensor signal or baseline with operating temperature can give useful diagnostic information. Such measurements may require the application of target gas, or in some cases can be performed in ambient air—for example the analysis of the baseline resistance of metal oxide sensors as a function of temperature.

Performing temperature studies on the behaviour of heated sensors requires some means of varying the sensor temperature in a controlled way. For catalytic bead 'pellistor' devices operated in a detector/compensator bridge circuit this may simply involve varying the voltage applied to the bridge rather than specifically setting to particular temperatures. For pellistors or metal oxide sensors operated in constant temperature circuits some means of closed loop control is required to adjust the power to maintain the required temperature. This could be achieved using a PC based data acquisition system with digitally controlled power supply. However, such systems as discussed above are not cost effective candidates to incorporate into a docking station.

For heated gas sensors, as described earlier, the heater control circuit in the instrument may be a simple non-adjustable single temperature control which may have no measurement capability, and is likely to be optimised for operation at a single temperature at minimum cost with maximum stability. An external circuit, in a docking station, can be used to analyze the temperature dependence of the sensor behaviour by performing heater control and/or measurement.

Infrared gas sensors typically use a filament lamp as a source and two detectors responding to different wavelengths as 'sensing' and 'reference' channels. Although changes in the absolute intensity of the source are compensated by the ratiometric measurement of the 'sensing' and 'reference' channels, changes in the spectral output or 'colour temperature' of the source gives rise to changes in the relative signals on the two detectors resulting in shifts in the sensor baseline and/or sensitivity.

When using a filament lamp, changes in spectral output occur over time as the lamp ages. Some sensors overcome this problem by having two 'reference' channels with wavelengths either side of the 'sensing' wavelength to compensate for effects of changes in spectral output, but this requires an additional detector and circuitry and hence increases cost.

The dependence of spectral output on lamp filament temperature can be described by well known characteristic curves such as those for black body radiation. By varying the lamp drive voltage/intensity/filament temperature in a controlled manner and monitoring the changes in the signals from the detectors, this behaviour can be characterized and compensated/corrected for as appropriate.

In a disclosed embodiment, drift in lamp spectral output can be corrected without obtaining a detailed characterization of its behaviour. In this embodiment, it is not necessary to use a separate spectrometer. The existing source and reference channels in the sensor can be used as a simple 2-wavelength spectrometer. It may still be desirable to perform more detailed measurement/control analysis than is present in the portable instrument—for example the lamp drive voltage in the instrument may be fixed at constant voltage or power whereas it is necessary to be able to adjust this drive signal in order to perform the characterization. Similarly, more sophisticated measurement electronics and/or signal processing may be required than is normally present in the instrument. As needed, such circuitry and functionality can be incorporated into a docking station which embodies the invention.

Infrared sensors typically use a pulsed or AC modulated light source and therefore require the use of some form of AC detection circuitry. Changes in the shape of the signal received from the detector(s) can affect the accuracy of the measurement as well as offering some diagnostics into the performance of the source and or detector. For example, the rise and fall time of the signal are dependent on the thermal time constant of the lamp as well as capacitance within the detector and associated circuitry. Analysis of the pulse waveforms would typically be performed with a digital storage oscilloscope or frequency response analyser.

Measurement of pulse waveforms would require more sophisticated electronics and signal processing than would normally be present in a hand held instrument—which would normally just measure the amplitude of the AC signal using a lock in amplifier or suitable filtering and rectification circuit. However analysis of a pulse (which would typically have a frequency of a few hertz) would not require very large bandwidth—1 KHz may be sufficient. Therefore a relatively low cost analogue-to-digital convertor and programmable processor with associated executable control software could be incorporated into the docking station to perform the measurement.

Those of skill in the art will understand that while the above discussion has focused mainly on diagnostic techniques to be performed on sensors, it can also beneficial to be able to perform diagnostics on sensor measurement circuitry within the instrument, for example to correct for component value drift, offset voltage etc, possibly allowing the use of lower tolerance, less expensive, components in the instrument. In accordance with the above, impedance spectroscopy could also be used to perform tests on the sensor measurement electronics in the instrument—for example the behaviour of certain components such as capacitors in the measurement electronics for infrared sensors is quite important. Having the ability to measure and possibly compensate for drift in capacitance in a filter circuit may allow lower cost and/or physically smaller capacitors to be used in such circuits. Further, in other embodiments, many of the above techniques could be used in combination with each other—for example Impedance Spectroscopy could be performed as a function of bias voltage on an electrochemical sensor or as a function of operating temperature on a heated metal oxide sensor.

FIG. 1 is a block diagram of a docking station 10 which embodies the present invention. Station 10 has a housing 12 which defines an instrument receiving port 14. Station 10 can include a singular port 14, or a plurality, 14a, d . . . I of ports, some of which could be different than others, all without limitation.

An instrument I which includes one or more gas sensors Si can releasibly engage the port 14. Evaluations of the parameters of the instrument I, which could include some of the above described cost-effective processing, can be automatically carried out by the docking station 10. The station 10 can also provide a test gas sample(s) via interface 20 to the instrument I for calibration and other tests. Station 10, via closed loop recharging circuits 22 can automatically recharge a battery, or batteries of the instrument I.

The port 14 can include an interface 34 which can wirelessly, or, mechanically and electrically releasibly engage an interface IF of the instrument I. Various types of inductive or non-contact interfaces come within the spirit and scope of the invention. Alternately, if battery or, non-battery power sources are used to power the instrument, for example fuel cells, interface 34 can be used to evaluate them via a wired or wireless connection.

The interface IF can be a universal interface common to a plurality of different instruments. The instrument I can include circuits C which couple the sensor(s) Si to the interface IF as well as implement predetermined functionality of the instrument.

Docking station 10 can also include control circuits 28 implemented at least in part by a programmed processor 28a and associated control software 28b. Software 28b can be stored on a computer readable medium which is accessible by the processor 28a. Processor 28a, when executing software 28b can carry out some or all of the above noted limited function evaluations of the instrument I.

Station 10 can also include test circuitry 30 (to test or carry out evaluation of instrument I), one or more analog-to-digital converters 32 (to acquire data from instrument I), both of which can communicate with the instrument I via port interface circuits 34. Docking station 10 can also include a data storage unit 38, for example semiconductor storage, magnetic storage, or optical storage, on which can be stored cumulative data as to the instrument I as well as other instruments which have been processed by the station 10 over a period of time. Control software 28b can carry out comparison processing of various types between currently detected parameters of the instrument I and parameter values previously detected over a period of time.

Station 10 can also include an input/output interface 42 which can provide a wired or wireless bidirectional communication capability, via a wireless communication system, or via a computer network N, such as the Internet, with a displaced monitoring facility F.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. A docking station comprising:
a housing, the housing defines at least one gas detector receiving port, the receiving port includes at least one of a wired or a wireless integrated interface to communicate with a detector to be evaluated;
control circuits carried by the housing and coupled to the integrated interface where the control circuits carry out limited, predetermined detector evaluations the control circuits coupling at least a pulse signal to the detector;
a gas control interface carried by the housing and coupled to both the control circuits and the integrated interface, the gas control interface providing a selected gas sample to a detector in a receiving port via the integrated interface, and where the control circuits in conjunction with varying operating parameters of a sensor in the port activate the gas control interface to provide the gas sample; and
the integrated interface coupling electric signals from the control circuits and a test gas sample from the gas source to the docking station and wherein the control circuits analyze at least decay transients of the pulse signal to measure factors relating to electrodes, electrolyte and mass transport.

2. A docking station as in claim 1 where the integrated interface includes a plurality of electrical contacts for releasably engaging the detector to be evaluated.

3. A docking station as in claim 1 where the control circuits carry out at least one of a limited, predetermined, form of impedance spectroscopy to perform diagnostics on a sensor in the detector, or to perform diagnostics on a power source in the detector, or to measure resistance of a heater for the detector, or to measure sensor output signals in response to varying sensor bias voltage, or to evaluate performance of sensor measurement electronics of the respective detector.

4. A docking station as in claim 1 which includes circuitry to carry out heater control and measurement of a detector having a heated sensor.

5. A docking station as in claim 1 which includes circuitry coupled to source and reference channels of an infrared-type detector in the receiving port.

6. A docking station as in claim 1 which includes circuitry to carry out a narrow bandwidth pulse measurement of an infrared sensor in the detector in the receiving port.

7. A docking station as in claim 1 which includes circuitry to carry out diagnostic evaluations of measurement circuitry of a detector in the receiving port.

8. A docking station as in claim 1 which includes a storage unit and a stored data base of information relating to previously tested detectors, the storage unit, coupled to the control circuits, provides a computer readable medium which carries the data base.

9. A docking station as in claim 8 where the control circuits include a programmable processor coupled to the storage unit, the information is accessible to the processor to evaluate electrical condition indicating signals being received from a detector in the receiving port.

10. A docking station as in claim 1 where the control circuits evaluate at least one parameter of a detector power supply.

11. A docking station as in claim 10 which include recharging circuitry carried in the housing and coupled to the integrated interface and control circuitry, the recharging circuitry providing electrical energy to the detector power supply via the integrated interface.

12. A docking station as in claim 10 where the control circuits evaluate a parameter of at least one of a detector battery or a fuel cell.

13. A gas detector docking station comprising:
a housing which includes a plurality of gas detector receiving ports, one of the ports includes an associated instrument interface which can releasably engage members of a family of different gas detectors, the different members of the family each exhibit a common interface which engages the instrument interface when the respective detector is inserted into the port;
control circuits which include a programmable processor and associated control software, stored on a computer readable medium, to selectively carry out a plurality of detector evaluations including evaluating performance of sensor measurement electronics of the respective detector the control circuits coupling at least a pulse signal to the respective detector;
a gas sample control interface carried by the housing and coupled to both the control circuits and the instrument interface, the gas control interface providing a selected gas sample to members of a family of different gas detectors via the instrument interface, and where the control circuits in conjunction with varying operating parameters of a sensor in the ports activate the gas control interface to provide the gas sample; and
the instrument interface coupling electric signals from the control circuits and a test gas sample from the gas source to the family of different detectors being evaluated and wherein the control circuits analyze at least decay transients of the pulse signal to measure factors relating to electrodes, electrolyte and mass transport.

14. A docking station as in claim 13 which includes data storage circuitry, coupled to the control circuits, the storage circuitry carrying time varying, previously stored, detector information indicative of prior evaluations of respective detectors.

15. A docking station as in claim 14 where the instrument interface includes one of a wired interface for communicating with a detector or a wireless interface for communicating with a detector.

16. A docking station as in claim 13 where the control circuits evaluate at least one parameter of a power supply of at least one member of the family of different detectors being evaluated.

17. A docking station as in claim 16 where the control circuits evaluate a parameter of at least one of a battery or a fuel cell of at least one member of the family of different detectors being evaluated.

18. A docking station as in claim 13 which include recharging circuitry carried in the housing and coupled to the instrument interface and control circuitry, the recharging circuitry providing electrical energy to the power supply of at least one member of the family of different detectors being evaluated via the instrument interface.

19. A docking station as in claim 13 where the control circuits carry out at least one of a limited, predetermined, form of impedance spectroscopy to perform diagnostics on a sensor in at least one member of the family of different detectors being evaluated, or to perform diagnostics on a power source in at least one member of the family of different detectors being evaluated, or to measure resistance of a heater for at least one member of the family of different detectors being evaluated, or to measure sensor output signals in response to varying sensor bias voltage, or to evaluate performance of sensor measurement electronics of a respective member of the family of different detectors being evaluated, the control circuits couple at least a pulse signal to the at least one member and analyze at least decay transients of the pulse signal to measure factors relating to electrodes, electrolyte and mass transport.

* * * * *